United States Patent
Cooke et al.

(10) Patent No.: US 6,190,415 B1
(45) Date of Patent: *Feb. 20, 2001

(54) DEEP FLEXION KNEE PROSTHESIS

(76) Inventors: T. Derek V. Cooke, P.O. Box 91877, King Fahad Road, Olaya Riyadh (SA), 11643; Bryan Cornwall, 926 First St., Unit #1, Hermosa Beach, CA (US) 90254

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/053,325

(22) Filed: Apr. 1, 1998

(30) Foreign Application Priority Data

Apr. 4, 1997 (CA) .................................. 2201799
Mar. 26, 1998 (CA) .................................. 2233265

(51) Int. Cl.[7] ........................................ A61F 2/38
(52) U.S. Cl. .................................. 623/20.33; 623/20.31
(58) Field of Search ..................... 623/20, 20.36, 623/20.35, 20.34, 20.33, 20.32, 20.31, 20.3, 20.29, 20.28, 20.27

(56) References Cited

U.S. PATENT DOCUMENTS

| 4,586,933 | * | 5/1986 | Shoji et al. | 623/20 |
| 4,808,185 | * | 2/1989 | Penenberg et al. | 623/20 |
| 4,944,756 | * | 7/1990 | Kenna | 623/20 |
| 5,358,530 | * | 10/1994 | Hodorek | 623/20 |
| 5,800,552 | * | 9/1998 | Forte | 623/20 |
| 5,871,539 | * | 2/1999 | Pappas | 623/20 |
| 5,871,542 | * | 2/1999 | Goodfellow et al. | 623/20 |

* cited by examiner

Primary Examiner—David J. Isabella
Assistant Examiner—Alvin Stewart
(74) Attorney, Agent, or Firm—Pearne & Gordon LLP

(57) ABSTRACT

A knee prosthesis, includes a femoral element, a tibial element and at least one bearing element between the femoral and tibial components. The femoral component has medial and lateral condylar elements that extend posteriorly about 160°.

8 Claims, 3 Drawing Sheets

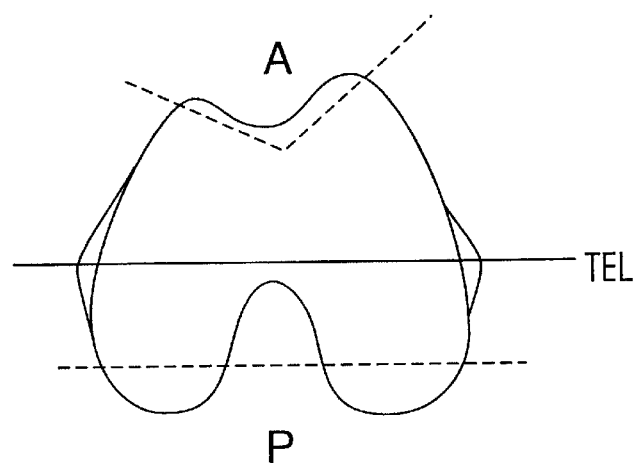
FIG. 4
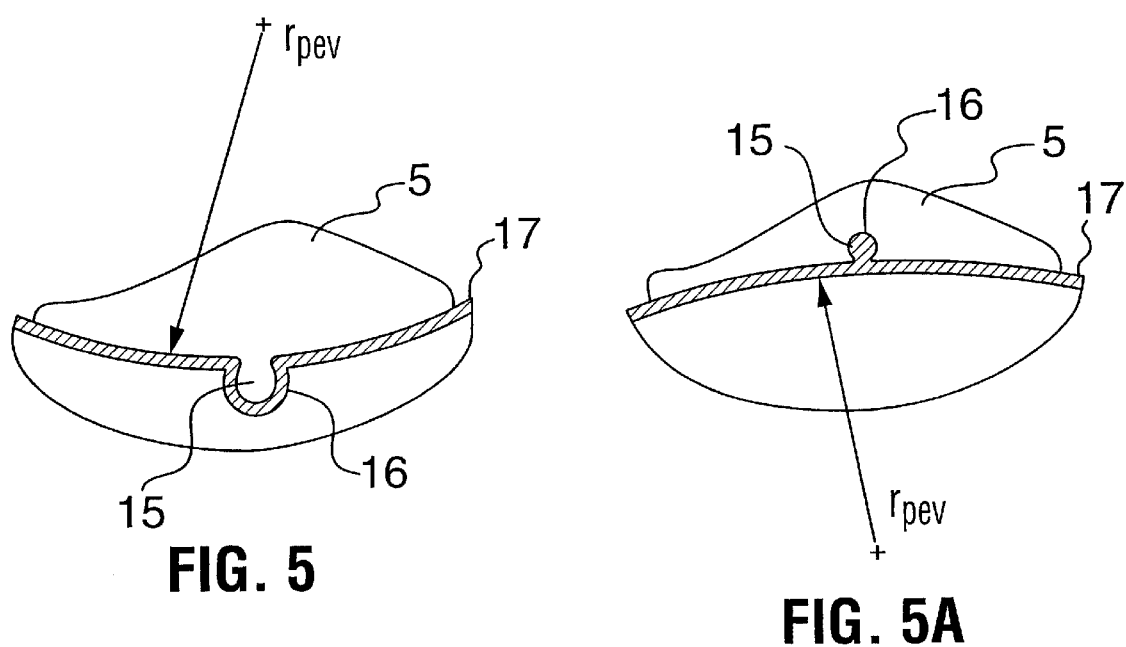
FIG. 5
FIG. 5A

DEEP FLEXION KNEE PROSTHESIS

FIELD OF THE INVENTION

The present invention relates to the field of orthopaedics. In particular, the present invention provides a prosthetic knee kinematically and anatomically resembling a human knee, and providing a user thereof with enhanced flexion capability as compared to other currently available knee prosthesis.

BACKGROUND OF THE INVENTION

A knee is made up, essentially, of four composite parts. The most distal portion is the tibia, which is the larger of the two lower leg bones. The upper surface of the tibia is a generally horizontally oriented plateau. Lining the proximal tibial and distal femoral surfaces are the second important part of the knee, the cartilaginous bearing surfaces, upon which physically rests the distal surfaces of the third portion of the knee, the femoral condyles. Each condyle (the medial, or inward one, and the lateral, or outward one) is generally a toroidal projection on the end of the femur, that can rotate over the bearing surfaces on the tibia. To achieve a wide range of flexion, however, the condyles do not simply rotate on the tibia. They also slide in an anterior and posterior direction, and then revolve generally latero-medially about a centero-medial zone on the tibial plateau. The patella, the fourth part of the knee, in a muscle-tendon mechanism contacts the condyles anteriorly, acting as a pulley for enhancing knee extension. To prevent the femur from sliding off the tibia, the patella is positioned anteriorly of the condyles, between them and connected to the tibia and femur by the patellar tendons and quadriceps muscles respectively.

Prior art prosthetic knee designs have accounted reasonably well for limited rotation and posterior-anterior sliding. For instance, in U.S. Pat. No. 5,282,868 (Bahler) there is described a prosthetic knee that specifically addresses the need for the femoral prosthetic to slide anteriorly while it rotates. The femoral part may, moreover, revolve slightly about its central longitudinal axis. This feature, however, does not enhance flexion. Accordingly, the Bahler knee, while advanced in view of prior designs, does not approach anatomical flexion criteria.

Similarly, in U.S. Pat. No. 5,314,483 (Wehrli et al) a knee prosthesis is described which is capable of sliding and rotation, and which is capable of limited rotation about a centrally located axis. It is similarly limited in flexion.

It is the object of the present invention to provide a prosthetic knee that flexes over a range approximating ordinary knee flexion. In particular, an object of the present invention is to provide a knee capable of flexion in the range of approximately 160°, which represents an enhanced flexibility of 25°–45° over currently available prosthetic knees.

A further object of the present invention is to provide a femoral prosthesis that is exceptionally stable after implantation.

In a broad aspect, then, the present invention relates to a knee prosthesis, including: a femoral element; a tibial element; and at least one bearing element between said femoral and tibial component said femoral component having medial and lateral condylar elements that extend posteriorly about 120°.

BRIEF DESCRIPTION OF THE DRAWINGS

In drawings that illustrate the present invention by way of example:

FIG. 4 is a schematic view of the distal end of a femur, showing bone cut lines, relative to the trans-epicondylar line of the femur; and FIGS. 5 and 5A are cross-sectional view of patellar lining components of the present invention, which are overall anatomically shaped.

DETAILED DESCRIPTION

Figure 1:
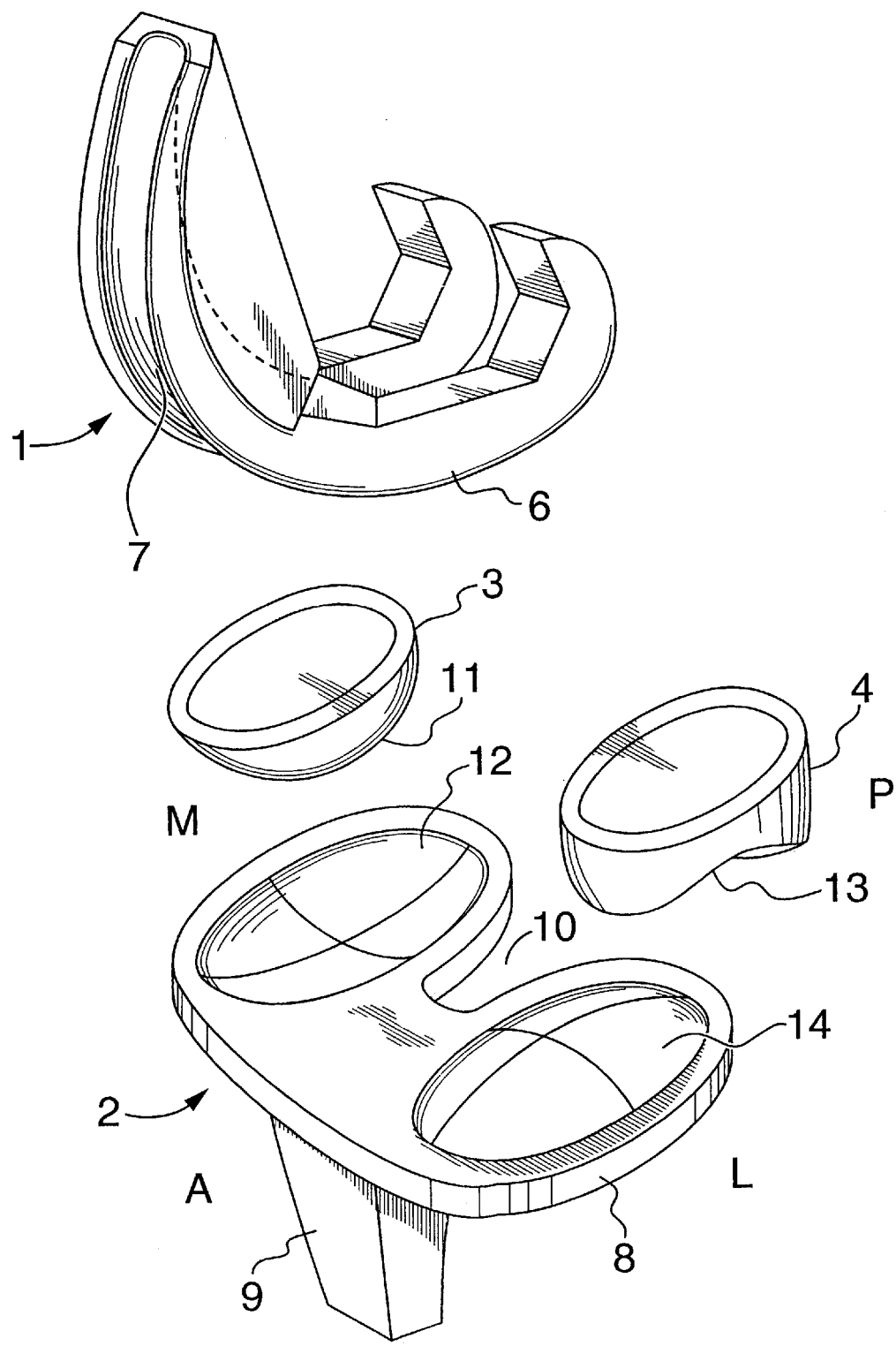
FIG. 1 is an exploded view of a knee prosthesis according to the present invention.
Figure 2:
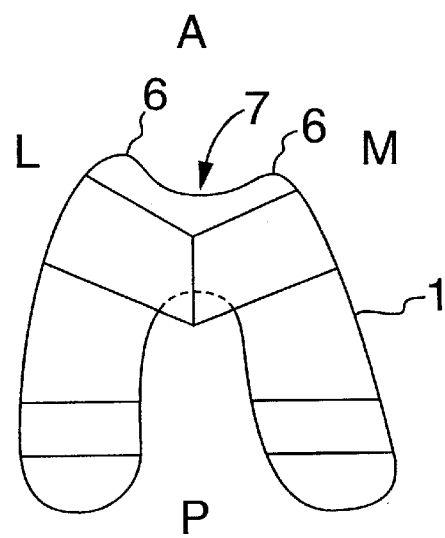
FIG. 2 is a top view of the femoral component of FIG. 1.

As FIG. 1 of the drawings illustrates, the present invention provides a prosthetic knee including a femoral condylar element 1, a tibial plateau element 2, a bearing element that may be in one or two pieces 3,4, and a patellar lining 5 (see FIGS. 5 and 5A). In many instances, such as is illustrated in FIG. 1, the patella does not require the lining of the present invention.

The femoral component 1 has condylar bearing surfaces 6 that extend posteriorly a far greater extent than those on prior art femoral prosthesis.

Figure 3:
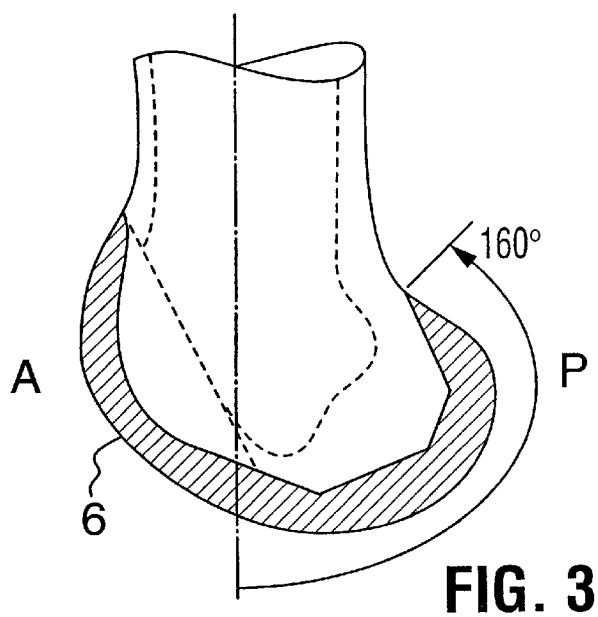
FIG. 3 is a sectional view, through a condyle, of the component of FIG. 2, showing bone cut pattern.
Figure 3A:
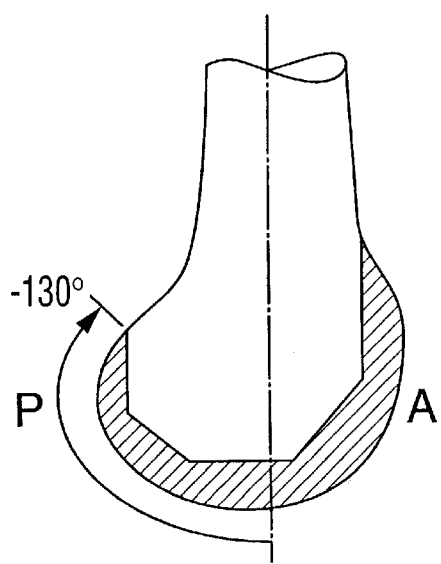
FIG. 3A is a view similar to FIG. 3, showing the orientation of a prior art femoral component to the longitudinal axis of the femur.

As shown in FIG. 3A, the condylar bearing surfaces on a typical prior art femoral prosthesis extend posteriorly about 130° from the longitudinal axis of the femur. The reason for this limitation is the convention of cutting the femur parallel to its longitudinal axis. As is clear from FIG. 3A, such a cut pattern permits the femoral prosthesis to be slid onto the femur, but does not permit posterior condylar bearing beyond about 120°. In the prosthesis of the present invention, however, as shown in FIG. 3, the condylar bearing surfaces 6 extend much further posteriorly, to about 160° from the longitudinal axis of the femur. This permits the rotation of the femur on the tibial plateau over a greater arc, for enhanced knee flexion. As can be observed from FIG. 3 of the drawings, however, in order for the femoral prosthesis to be fitted on the femur, the end of the femur is cut to a profile conforming to the interior of the prosthesis. Since the prosthesis must be slid over the end of the femur, however, the inner anterior and posterior surfaces of the prosthesis must be parallel or divergent. Therefore, the implant is applied in an orientation of flexion at a specific angle of about 20°–30° typically about 25° with respect to the femoral shaft, thereby providing full posterior condylar coverage as well as coverage of the distal anterior parts. The femoral component also provides a deeply set anatomically curved anterior central and distally placed groove 7 for appropriate articulation and accommodation of the patella throughout the flexion range. This articulation begins as the patella enters the groove at the start of flexion with zonal contact and at terminal flexion with two regions of contact medially and laterally for the condylar separations beyond the intracondylar notch. (The notch anatomically separating the condyles and providing attachment of the cruciate ligaments to the femur.)

Figure 3B:
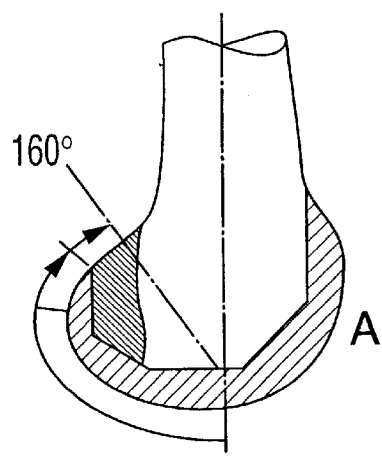
FIG. 3B is a view similar to FIG. 3, showing an alternative embodiment of the femoral component of the present invention.

An alternative, but less desirable embodiment of the femoral component of the present invention is shown in FIG. 3B. This embodiment, which permits a more or less conventional cutting orientation. In this embodiment, the posterior condylar portion of the femoral component is thickened, as shown in FIG. 3B, whereby the posterior condyle is extended to permit 160° of rotation. The disadvantage of this embodiment is possibly excessive bone loss. However, it may be appropriate for use with some individuals, especially elderly persons, for whom a simplified surgical procedure would be desirable.

The femoral component has suitably curved condylar surfaces, generally rounded posteriorly for matching interface with plastic bearings whose form and extent provides conforming contact with the femoral condyle over the entire posteroproximal articular regions (uncovered in current designs) and vitally needed to provide full flexion.

The tibial base plate 8 is generally flat and more or less oval outline having a central stem 9 of a conventional design for bone fixation, and a postero-central cut-out 10 to preserve the posterior cruciate ligament (PCL) and as needed, the anterior cruciate ligament (ACL). Its articulating surface for a plastic bearing is uniquely formed to match the asymmetric anatomic geometry of the medial and lateral femuro-tibial compartments.

In FIG. 1, it will be seen that the interface of the plastic bearings 3,4 with the femoral condyles is conforming such that the posterior-distal convexity of condyles mates against concavities of each bearing with sufficient clearance to allow only a jog of displacement but ease of sliding rotation. Each medial and lateral plastic part 3,4 articulates with the tibial base plate separately in such a way as to provide (A) MEDIALLY mainly loading and some limited sliding, rotation motion between convex distal plastic surfaces 11 and matching concave proximal tibial surface 12, the radius of curvature of same bearing plastic-tibial interface being greater than the matched radii defined in curved surfaces of femur and bearing, and (B) LATERALLY extended motion in which said bearing's distal surface 13 is concave to match a gently rounded convex surface 14 of the lateral tibial eminence whose radius is greater than the matched more proximal bearing femoral surface. The convex-concave medial (dished) interactive with the concave, convex lateral (compressed dumbbell form) bearings provides a means for rotation of the bearings on their tibial surfaces, and to each other and, by nature of conforming contact with the femur they thereby provide for femoral rotation about a natural anatomic axis located centero-medially.

The provision of axial rotation restores the requirement for normal knee motion seen in full extension as 'locking home' means for external tibial rotation, axial rotation in gait and of critical importance for these embodiments, internal tibial rotation during terminal parts of deep flexion.

In the preferred embodiment, the bearings are made of plastic shaped much as discs, medial being concave, convex (proximally—distally) and lateral convex-concave (dumbbell shape), having varying thickness of plastic and with the contour margins of bearings extending sufficiently anterior and posteriorly combined with the large surface areas to provide for stability once inserted between elastically separated articulating surfaces of femur and tibia. Such elastic separation is the natural occurrence due to intact collateral, posterior cruciate and capsular structures. These are further supported by musculotendinous structures coopting joint surfaces and also providing motion. This design affords a 'self-orienting' mechanism for bearing location between articulating metal parts.

This embodiment is highly reliant on carefully balanced soft tissues and will have most stability in circumstances when both Anterior cruciate ligament (ACL) as well as Posterior cruciate ligaments (PCL) may be preserved.

The plastic bearings 3,4 may be shaped distally in the form of a dovetail (not illustrated) whose form is curved in horizontal plane towards the center of rotation in the midcondylar portion of the tibia and curved in a second dimension orthogonal to the first (mainly sagittal) to fit a matched female groove in medial and lateral tibial parts. Such captive mechanisms are designed to restrict sideways motion enough to prevent escape of the bearing. But, the tolerance of surfaces are such as to allow free sliding motion of the bearing in its curved dovetail groove, forwards and backwards and in part circular to radius center. This embodiment is of greater application in arthritic cases that lack an ACL and/or a PCL. The sagittal curves have the same orientation of radius centres (opposite each other) as in unrestricted form.

In a total knee replacement the patella may or may not be resurfaced. In the latter event a resurfacing design is provided by the present invention that will articulate in a zonal congruent pattern with the antero-distal circular femoral groove by a matching congruent surface plastic bearing. During maximal flexion the patella angle with respect to the femur changes and would induce 'lift-off' of said bearing if rigidly fixed to the cut bone posterior surface of the patella. Therefore, the design is such to allow a small element of motion, in three directions between the plastic bearing 5 and a dish-shaped metal base plate 17 attached to the patella. In one form (FIG. 5) the radius of curve is designed greater than the radius of the patella groove convex plastic to concave metal patella base plate. In another (FIG. 5A), a reversed configuration is described, concave plastic to convex metal base plate. These options may be chosen to best fit the nature of available bone stock. To prevent bearing dislodgement, a captive mechanism is designed as a central 'collar stud' 15 of plastic that snaps into a centrally located recess 16 in the metal base plate 17. Sufficient clearance is provided between the opening margin and neck of the plastic collar to permit motion. Alternatively, as shown in FIG. 5A, the stud 15 may be formed in the base plate 17, and the recess in the patella prosthesis 5.

In a further embodiment (not illustrated), a design configuration is provided for posterior cruciate substitution. In this situation, the bearings for the medial and lateral tibiofemoral articulation will be as described above. However, the design for both the femoral and tibial components differs in the incorporation of a posterior cruciate substitution post, found at the central posterior aspect of the tibial baseplate, to interact with a suitably shaped femoral housing located within the intercondylar area of the femoral component. The tibial post and femoral receptacle have articular bearing contacts to engage in flexion, beyond and up to maximum flexion, and are oriented such that the bearing allows for and encourages tibial internal rotation in deep flexion while constraining abnormal posterior displacement of the tibia. The bearing of the substitution mechanism will be a plastic material of the tibial post and metal for the femoral receptacle. This alternative embodiment of the present invention makes it possible to adapt the essential aspects of the present invention to prosthesis designs that sacrifice the cruciate ligaments.

It will be understood, moreover, that although a total knee replacement is described, it is feasible to utilize only a portion of the prosthesis. For instance, if only either the medial, or lateral condyle is damaged, it is not necessary to replace both. Any portion of the present invention may be used independently of the other. In particular, all medial components, or all lateral components may be implanted, without affecting the remainder of the knee.

It is to be understood that the examples described above are not meant to limit the scope of the present invention. It is expected that numerous variants will be obvious to the person skilled in the field of orthopaedic prosthesis design without any departure from the spirit of the invention. The appended claims, properly construed, form the only limitation upon the scope of the invention.

What is claimed is:

1. A femoral knee prosthesis comprising a lateral and a medial condylar element, and an intermediate portion joining said condylar elements, said condylar elements and said intermediate portion having interior surfaces and exterior surfaces, said exterior surfaces of the posterior aspect of said condylar elements extending proximally more than 140° relative to the longitudinal axis of a femur for which a said prosthesis is intended, and the interior surfaces of said posterior portion of said condylar element being substantially planar, and converging proximally toward said longitudinal axis; said intermediate portion being located between the anterior portions of said condylar elements, and having an interior surface in two portions that meet along a crest substantially parallel to, or proximally divergent from, said interior posterior surfaces of said condylar elements, said two portions of the anterior interior surface of said intermediate portion each being planar, and extending from said crest to the lateral or medial edge respectively of the adjacent anterior portion of a said condylar element.

2. A prosthesis as claimed in claim 1 wherein said exterior surfaces of the posterior aspects of said condylar elements extend posteriorly more than about 150° relative to the longitudinal axis of a femur for which the prosthesis is intended.

3. A prosthesis as claimed in claim 1 wherein said exterior surfaces of the posterior aspects of said condylar elements extend posteriorly more than about 160° relative to the longitudinal axis of a femur for which the prosthesis is intended.

4. A prosthesis as claimed in claim 1, wherein the exterior surfaces of said condylar elements are smoothly rounded, and the interior surfaces are defined by a series of flat transition surfaces extending around the inner periphery of said condylar elements, from said interior posterior surfaces to said interior surfaces of said intermediate portion.

5. In combination, a femoral prosthesis as claimed in claim 1, an implantable tibial plateau prosthesis and a pair of bearing elements each having an upper surface and a lower surface, between said femoral prosthesis and said tibial prosthesis.

6. The combination of claim 5, wherein said tibial prosthesis is provided with a plate-like plateau including upwardly facing medial and lateral articular surfaces adapted to receive said bearing elements.

7. The combination of claim 6 wherein said lateral articular surface of said tibial prosthesis is convex, and the bearing for insertion between said lateral articular surface of said tibial prosthesis and the lateral condylar element of said femoral prosthesis has concave upper and lower surfaces, to permit said lateral condylar element to slide rotationally in an anterior to posterior direction during flexion of a knee in which said combination is implanted, without dislodging said bearing.

8. The combination of claim 7, wherein said medial articular surface of said tibial prosthesis is concave, and the bearing for insertion between said medial articular surface of said tibial prosthesis and the medial condylar element of said femoral prosthesis has a concave upper surface, and a convex lower surface to permit said medial condylar element to turn relative to said medial articular surface of said tibial prosthesis during flexion of a knee in which said combination is implanted.

* * * * *